(12) United States Patent
Bolleter et al.

(10) Patent No.: US 11,229,506 B2
(45) Date of Patent: Jan. 25, 2022

(54) CERAMIC IMPLANT

(71) Applicant: DENTALPOINT AG, Zürich (CH)

(72) Inventors: Philip Bolleter, Schlieren (CH); Pascal Wettstein, Villmergen (CH); Maximilian Warhanek, Zürich (CH)

(73) Assignee: DENTALPOINT AG, Zurich (CH)

( * ) Notice: Subject to any disclaimer, the term of this patent is extended or adjusted under 35 U.S.C. 154(b) by 432 days.

(21) Appl. No.: 16/062,982

(22) PCT Filed: Dec. 15, 2016

(86) PCT No.: PCT/EP2016/081317
§ 371 (c)(1),
(2) Date: Jun. 15, 2018

(87) PCT Pub. No.: WO2017/103026
PCT Pub. Date: Jun. 22, 2017

(65) Prior Publication Data
US 2018/0360572 A1  Dec. 20, 2018

(30) Foreign Application Priority Data

Dec. 17, 2015  (CH) .................................... 01848/15

(51) Int. Cl.
*A61C 8/00* (2006.01)
*A61C 13/083* (2006.01)
*A61L 27/10* (2006.01)

(52) U.S. Cl.
CPC .......... *A61C 8/0012* (2013.01); *A61C 8/0066* (2013.01); *A61C 13/083* (2013.01); *A61L 27/10* (2013.01)

(58) Field of Classification Search
CPC ...... A61C 8/0012; A61C 8/0066; A61C 8/006
See application file for complete search history.

(56) References Cited

U.S. PATENT DOCUMENTS

2010/0119995 A1* 5/2010 Grant ..................... A61C 8/005
433/174
2010/0196850 A1* 8/2010 Konig ................... A61C 8/005
433/173

(Continued)

FOREIGN PATENT DOCUMENTS

| EP | 1 352 619 A1 | 10/2003 |
| JP | 2013-509919 A | 3/2013 |
| WO | WO 2008/022635 | 2/2008 |

*Primary Examiner* — Ralph A Lewis
(74) *Attorney, Agent, or Firm* — Pauley Erickson & Swanson (57) ABSTRACT

A dental prosthesis system includes at least one first and second dental prosthetic care part (1, 2) made of zirconium dioxide ($ZrO_2$). Each of the two care parts has corner radii (R1, R11, R2, R22, R3, R26, R12, R13), and the corner radii (R1, R11, R2, R22, R3, R26, R12, R13) correspond to one another, wherein the first care part (1) is operatively connected to the second care part (2). At least one of the corner radii (R1, R11, R2, R22, R3) of the first dental prosthetic care part and/or the second dental prosthetic care part (R26, R12, R13) has a value of less than 0.1 mm, and the at least one corner radius (R1, R11, R2, R22, R3, R26, R12, R13) is produced by a material removal process using a laser method and/or by a machining process using a drill or a milling cutter made of full diamond.

20 Claims, 4 Drawing Sheets

(56) References Cited

U.S. PATENT DOCUMENTS

2014/0134570 A1     5/2014   Zipprich et al.
2014/0162210 A1*    6/2014   Thomke ............... A61C 8/0012
                                                          433/167
2017/0027669 A1*    2/2017   Baruc ................... A61C 8/006

* cited by examiner

Prior art

Fig. 4

Prior art

CERAMIC IMPLANT

BACKGROUND OF THE INVENTION

Field of the Invention

The invention pertains to an at least two-part dental prosthesis system of zirconium dioxide with a first and a second dental prosthetic care part, wherein the corner radii of these care parts are very small corner radii. The invention furthermore pertains to a method for producing these care parts.

Discussion of Related Art

Three machining techniques for zirconium dioxide are known from the prior art for the production of dental prosthesis systems. Hard-machining of the already sintered base body by means of diamond grinding is carried out in order to produce the desired geometric shape of the implant and the associated parts such as abutments, screws and pins.

In a second method for achieving the desired shape of the zirconium oxide body, it is machined in the form of a green body prior to the sintering operation, wherein this method is easier due to the lower hardness of the material. However, it was determined that a distortion of the zirconium dioxide occurs during the subsequent sintering operation and the required production tolerances can no longer be met. The sintered component therefore has to be reworked in order to realize the required narrow production tolerances.

This likewise applies to the third method known from the prior art in the form of an injection molding technique, in which an additional machining step, for example a grinding step, is required after the component has hardened in order to achieve the required precision in the production.

The dental implants and abutments realized by the applicant so far are made of zirconium dioxide (a high-strength material that is hot-isostatically compressed and doped with yttrium) and have corner radii of at least 0.25 mm, which are produced by hard-machining the already sintered zirconium dioxide by means of grinding.

Due to the anatomy of the human dentition, an implant has on average overall diameter of 3 to 6 mm such that the currently ground corner radii result in a diametric material loss between 0.4 and 0.6 mm. Another disadvantage of the grinding technique can be seen in the design of the internal bore of the implant. For example, an internal trihedron in the implant can currently only be ground with a corner radius of 0.4 mm because the realization of smaller radii proved to be economically unfeasible.

One reason for the restrictions in the grinding technique is that the abrasive particles break off preferentially on corner radii. The sharper or the smaller a corner radius should be designed, the faster the particles break off. Tools with radii smaller than 0.2 mm are therefore subjected to such high wear that an economical and dimensionally accurate production is hardly possible.

The design freedom in the construction of ceramic implants therefore has been in need of improvement for quite some time.

There is a particular need to realize small corner radii of the implants and the abutments in order to reduce the rotational clearance occurring between these two parts and to thereby improve the rotational stability of the abutment in the implant. In dental prosthesis systems produced so far, it was determined that the rotational clearance between the abutment and the implant on average amounts to about 5°, wherein this rotational clearance can be minimized accordingly by reducing the corner radii.

In addition to the three above-described methods for producing dental prosthesis systems, it is also known to use a laser material removal operation in the precision machining of ceramics. In dental technology, this method is used in the computer-assisted production of dental crowns.

EP1352619A1 describes a method of this type, in which it is proposed to use an ultrashort pulse laser for reconstructing the shape of the tooth as naturally as possible. The disclosed process is carried out in two stages. In a first step, a "rough machining" operation is carried out by means of cutting, wherein the surface design and the geometry of the ceramic blank are assimilated to the surface of the dental prosthesis to be produced. In the second step, the rest of the surface is gasified in an eroding fashion. Both machining steps, namely the cutting step and the eroding step, are realized with different operating modes of the laser.

SUMMARY OF THE INVENTION

The present invention is based on the objective of making available a dental prosthesis system of zirconium dioxide, which does not have the disadvantages of known dental prosthesis systems.

The invention furthermore aims to make available a method for producing dental prosthesis systems, by means of which very small corner radii of preferably less than 0.15 mm, particularly less than 0.10 mm, can be realized.

The present invention as characterized in the claims proposes a new solution to the above-described problem and the objectives derived therefrom.

In the following description, a dental prosthesis system refers to the following parts: a first and a second dental prosthetic care part, wherein the first dental prosthetic care part is a part that is anchored in the bone, e.g. an implant. The second dental prosthetic care part is a part that is connected to the first dental prosthetic part.

This includes: abutments, healing caps, impression copings and gingiva formers. This furthermore includes screws and pins that are designed for directly connecting the parts of the definitive or the provisional care to the implant. The implant and the parts connected thereto, particularly the abutment, are made of high-strength zirconium dioxide, which is hot-isostatically compressed and doped with yttrium.

The term base body used in connection with the method for producing the particularly small corner radii refers to a blank of already sintered zirconium dioxide, in which the desired corner radii are machined by means of a machining operation using a drill or a milling cutter of full diamond and/or an ultrashort pulse laser.

Corner radii arranged on the first dental prosthetic care part refer to the radii that correspond to, i.e. interact with or contact, corner radii arranged on the second dental prosthetic care part.

A drilling tool or milling tool of full diamond refers to a tool that consists of a polycrystalline diamond (PKD), a diamond produced by means of chemical vapor deposition (CVD) or a monocrystalline diamond (MKD). A diamond produced by means of chemical vapor deposition is a full diamond and not a tool that was merely coated with diamond by means of the CVD process.

In another alternative embodiment to a full diamond, the drilling or milling tool consists of cubic boron nitride (CBN).

An ultrashort pulse laser refers to a laser that emits pulsed laser light with a pulse duration in the range of picoseconds or less. It is a picosecond laser.

The starting material, in which the corner radii are inserted, is zirconium dioxide in the already sintered state. It is not a green body that is machined and subsequently subjected to a sintering process. The material used is yttrium-stabilized TZP ("tetragonal zirconia polycrystal"), TZP-A (partially yttrium oxide-stabilized zirconium oxide) and ATZ (alumina-reinforced zirconium oxide) with a Mohs hardness of approximately 8.

The difference between the grinding operation used so far and the milling or drilling operation implemented in the present invention can be seen in that the base body of sintered, hard zirconium dioxide is in accordance with the inventive method machined down. In this way, very time-consuming machining operations such as, for example, grinding a concave corner radius in a receptacle opening of an implant can be avoided. The machining of the sintered zirconium dioxide ceramic is then no longer subject to the restrictions of the grinding technique, but rather based on metalworking. The milling head used for the milling operation or the drilling head used for the drilling operation has a diameter of 0.5-5 mm and is made of full diamond, preferably a polycrystalline diamond. In comparison with a grinding tool, the milling head or the drilling head has a surface geometry that makes it possible to machine the zirconium dioxide ceramic. In this case, the surface geometry is realized in such a way that small corner radii of less than 0.15 mm, preferably less than 0.10 mm, can be realized on the base bodies.

The advantage of very small corner radii can be seen in that the remaining wall thickness, for example, in the production of an internal bore of the implant is greater than in the case of ground corner radii such that the mechanical stability of the implant is improved. This likewise applies to the design of an abutment stem.

Another advantage is the improved freedom in designing the dental prosthetic care parts. Due to the reduced material removal, this also results in a higher mechanical stability, improved handling in the positioning of the care parts, improved surgical freedom, improved freedom in the prosthetic care and therefore superior aesthetic results.

An advantage of using an ultrashort pulse laser can be seen in the contactless machining of the base body of zirconium dioxide. In comparison with a grinding operation, the machining tool is not subjected to any wear. This guarantees a high dimensional stability and therefore a precise production of the parts of the dental prosthesis system. This likewise applies to the use of a milling cutter or drill of full diamond. The low wear of these tools during the machining operation makes it possible to exactly produce the desired geometry.

Another advantage is the high dimensional stability achieved due to the contactless machining operation (and therefore no wear) in the case of a laser and the extremely low wear of the full diamond in the case of a milling operation.

The inventive dental prosthesis system comprises at least a first and a second dental prosthetic care part of zirconium dioxide ($ZrO_2$). Both care parts respectively have corner radii, wherein these corner radii correspond to one another in that the first care part is operatively connected to the second care part. At least one of the corner radii of the first dental prosthetic care part and/or the second dental prosthetic care part has a value of less than 0.15, preferably less than 0.1 mm, wherein the at least one corner radius is produced by means of a material removal operation using a laser and/or a machining operation using a drilling tool and/or milling tool of full diamond or cubic boron nitride.

In another embodiment of the invention, the at least one corner radius has a value between 0.05 mm and 0.1 mm.

In an embodiment of the inventive dental prosthesis system, the at least one corner radius of the first and/or the second dental prosthetic care part is a corner radius with concave geometry.

In another embodiment, at least one corner radius of the first and/or the second dental prosthetic care part has a shape that is sloped relative to a horizontal plane by 45°.

In another embodiment of the invention, the first dental prosthetic part is an implant and the corner radii of the implant correspond to the corner radii of the at least one second dental prosthetic care part, namely an abutment.

In another embodiment of the invention, the corner radii of the implant are formed by inner walls of a receptacle opening of the implant and the corner radii of the abutment are arranged on an abutment stem.

In another embodiment of the invention, the inner walls form an engagement key. The abutment stem comprises positioning elements, wherein the corner radii of the engagement key and the corner radii of the positioning elements correspond and the engagement key establishes a positive operative connection with the positioning elements such that the abutment can be positioned in the implant in a rotationally stable fashion. An engagement key refers to the part of the receptacle opening of the implant, which interacts with positioning elements that mare arranged on the abutment stem and realized, for example, in the form of projections, in order to thereby align the abutment relative to the implant. The corner radii arranged on the engagement key and the corner radii arranged on the positioning elements are referred to as indexing radii. In an embodiment, the engagement key is arranged on a distal end of the receptacle opening of the implant.

In another embodiment of the invention, the inner walls of the receptacle opening form an undercut and the abutment stem comprises fixing elements. The corner radii of the undercut and the corner radii of the fixing elements correspond. The undercut establishes a positive operative connection with the fixing elements such that the abutment can be fixed in the implant in an axial direction. The corner radii arranged on the undercut and the corner radii arranged on the fixing elements are referred to as groove radii. In the present context, an undercut refers to a part of the receptacle opening of the implant, which is arranged proximal to the engagement key. At least one fixing element arranged on the abutment stem engages into the undercut. The at least one fixing element is arranged on the abutment stem proximal to the positioning elements. When the abutment is connected to the implant, the fixing element engages into the undercut and the abutment is fixed in the direction of a vertical axis.

In another embodiment of the invention, the inner walls of the receptacle opening form at least one fitting cylinder opening and the abutment stem comprises a fitting cylinder. The corner radii of the fitting cylinder opening and the fitting cylinder correspond and the fitting cylinder and the fitting cylinder opening establish a positive operative connection such that a snug fit results between the two fitting cylinders.

In another embodiment of the invention, the receptacle opening of the implant comprises a circumferential edge with a corner radius, which is located in the distal direction.

In another embodiment of the invention, a corner radius extends circumferentially on the transition between the abutment head and the abutment stem.

In an inventive method for producing the inventive dental prosthesis system, the shape of the base bodies of the dental prosthetic care parts, particularly the shape of the corner radii, is produced with a drill and/or a milling cutter of full diamond or cubic boron nitride.

In another variation of the inventive method, the shape of the base bodies of the dental prosthetic care parts, particularly the shape of the desired corner radii, is produced by removing zirconium dioxide material with the aid of an ultrashort pulse laser.

In another variation of the inventive method, the corner radii of the engagement key of the implant and the corner radii of the positioning elements of the abutment are produced by removing the zirconium dioxide material with the aid of an ultrashort pulse laser.

In another variation of the inventive method, the base bodies of the dental prosthetic care parts are machined by means of a drilling and/or milling operation using a full diamond tool and in another step of the method by means of a material removal operation using an ultrashort pulse laser.

In a variation of the inventive method, a milling head with a tool diameter of 0.5 mm to 5 mm or a side-and-face milling cutter with a tool diameter of 5 mm to 20 mm is used for the milling operation.

In an inventive variation of the method for producing a dental prosthesis system, <=15% of the tool diameter are laterally advanced and a milling head with a tool diameter of 0.5-1.5 mm is used for a peripheral or a lateral milling operation, preferably for producing the corner radii of the second dental prosthetic care part.

In an alternative variation of the inventive method, a milling head with a tool diameter of 1.5-5 mm is used and <=10%, preferably <=7.5%, of the tool diameter are laterally advanced.

In another alternative variation, a side-and-face milling cutter with a tool diameter of 5-20 mm used and laterally advanced by <=10%, preferably <=5%, of the tool diameter.

In a peripheral or lateral milling operation, the depth of advance amounts to between 50 and 150% of the tool diameter.

In another inventive variation of the method, a milling head with a tool diameter of 0.5-1.5 mm is used for a groove milling operation, preferably for producing the corner radii of the first dental prosthetic care part, and advanced by an engagement depth of <=15% of the tool diameter.

In an alternative variation, a milling head with a tool diameter of 1.5-5 mm is used and advanced by an engagement depth of <=10%, preferably <=7.5%, of the tool diameter.

In another alternative variation, a side-and-face milling cutter with a tool diameter of 5-20 mm is used and advanced by an engagement depth of <=10%, preferably <=5%, of the tool diameter.

In a groove milling operation, the depth of advance amounts to between 50 and 150% of the tool diameter.

In a variation of the inventive method, a cutting speed of more than 100 m/min, preferably between 10-100 m/min, particularly between 25-50 m/min, is chosen for the milling operation. The advance lies between 400-1200 mm/min, preferably between 600-800 mm/min or preferably 100-600 mm/min, particularly between 200-400 mm/min. A cutting speed of 10-100 in/min, preferably 25-50 m/min, is chosen for the drilling operation. The advance lies between 5-75 mm/min, preferably between 10-20 mm/min. The drilling operation optionally takes place with chip removal such that increased heat development is avoided.

The inventive dental prosthesis system is produced with the above-described variations of the inventive method.

BRIEF DESCRIPTION OF SEVERAL VIEWS OF THE DRAWINGS

Exemplary embodiments of the invention are described in greater detail below with reference to the drawings. In these drawings.

DETAILED DESCRIPTION OF THE INVENTION

The production of the inventive dental prosthesis system, particularly the machining of the corner radii, is realized with the aid of an ultrashort pulse laser. In a preferred variation of the inventive method, the pulse duration of the ultrashort pulse laser amounts to 10 ps [picoseconds]. The laser used has an average output of 10 watt, a pulse frequency of 50 kHz-8.2 MHz and a wavelength of 1064 nm [nanometer]. In another preferred variation, the laser output amounts to 8 watt and the pulse frequency amounts to 100 kHz. An exemplary scanning speed of the laser lies at 100 mm/s.

In another variation, the production of the inventive dental prosthesis system is realized with the aid of a full diamond milling cutter and/or drill that is fixed in a conventional CNC milling machine. In an exemplary variation, the drilling operation is carried out with a cutting speed of 20 (m/min) and an advance of 2 mm/min. The drill used has a diameter, for example, of 1.8 mm and a length of 6 mm. In an exemplary variation, the milling operation is carried out with a cutting speed of 20 (m/min) and an advance of 200 mm/min. The milling cutter used has a diameter, for example, of 1.8 mm and a length of 3 mm.

In a preferred variation, the machining with the aid of an ultrashort pulse laser and the machining with the aid of a full diamond milling cutter/drill are combined.

Figure 1:
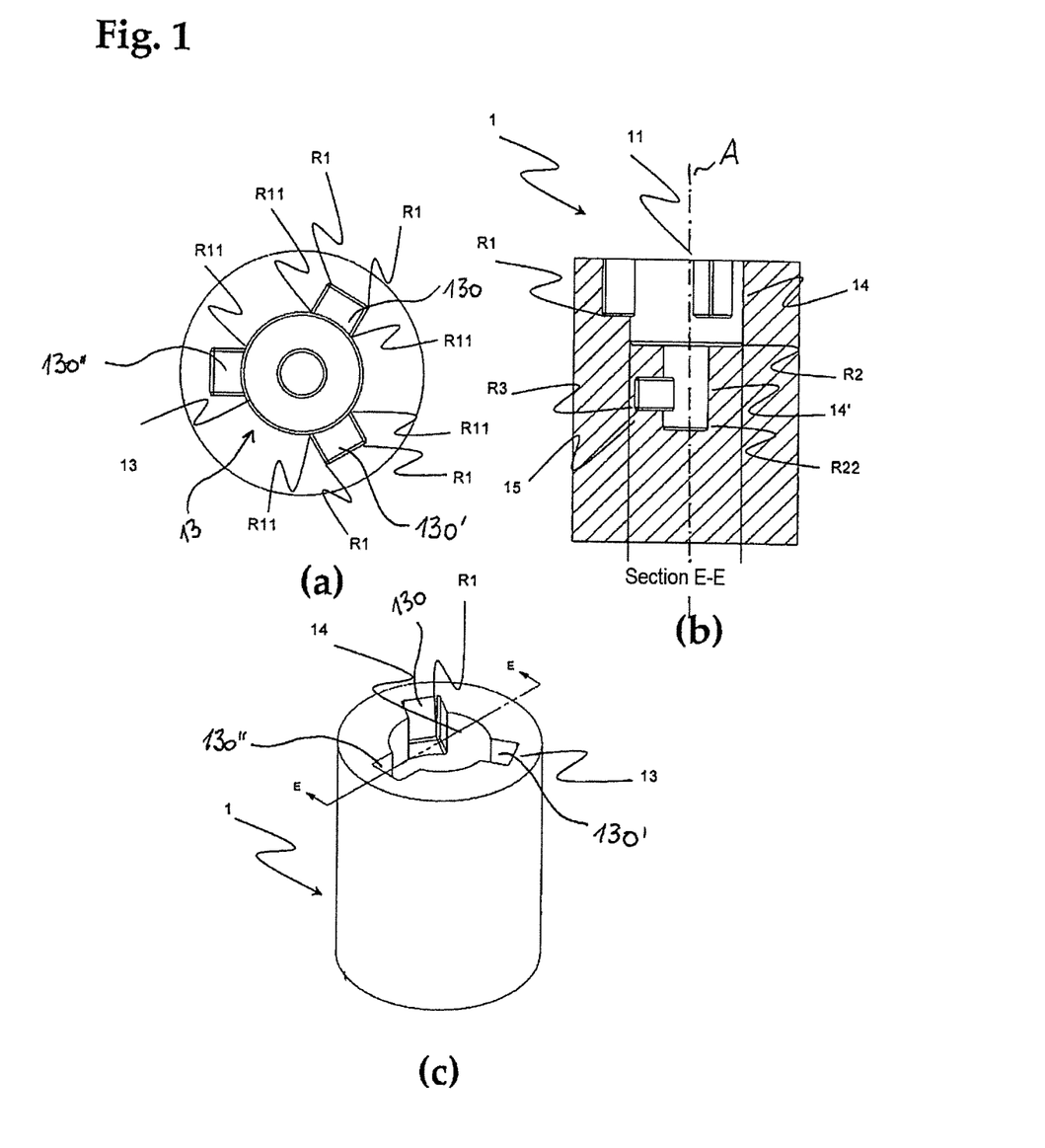
FIG. 1(a) shows a schematic top view into the receptacle opening of an implant.
FIG. 1(b) shows a schematic sectional view of the receptacle opening.
FIG. 1(c) shows a schematic perspective view, wherein only part of the implant is respectively illustrated in all three views 1(a)-1(c) such that, for example, an external thread for fixing the implant in the bone is not shown.

FIG. 1 schematically shows three different views (a), (b) and (c) of an embodiment of an implant 1 of zirconium dioxide ($ZrO_2$). Only part of the implant, particularly an exemplary embodiment of the internal geometry, is respectively illustrated in these views. An external thread, which implants typically comprise in order to be fixed in the jawbone, is not shown in FIG. 1.

The partially illustrated implant 1, particularly its internal geometry, was produced by means of a milling operation using a full diamond tool and/or by means of a laser material removal operation using an ultrashort pulse laser. The receptacle opening 11 of the implant has corner radii R1, R11, R2, R22 and R3 that are formed by the inner walls of the receptacle opening. In the embodiment illustrated in FIG. 1, the inner walls form an engagement key 13, two fitted cylindrical receptacle openings 14, 14' and an undercut 15. The corner radii R1 are arranged on the engagement key 13, the corner radii R2 and R22 are arranged on the fitting cylinders and the corner radii R3 are arranged on the undercut. The engagement key 13 serves for positioning an abutment (not illustrated in FIGS. 1(a)-(c)) in a rotationally stable fashion. In the embodiment illustrated in FIGS. 1(a), (b) and (c), the engagement key 13 is arranged on the distal end of the implant 1, wherein this engagement key is preferably formed by three engagement regions 130, 130' and 130". The corner radii R1 and R11 are arranged on the engagement regions 130, 130' and 130" of the engagement key. The corner radii R2, R22 and R3 lie proximal to the corner radii R1 and R11 referred to an axial direction (axis A). The corner radii R1 and R11 are so-called indexing radii. When an abutment (not shown in FIG. 1) is connected to the implant 1, these indexing radii correspond to additional indexing radii arranged on positioning elements of an abutment stem. The engagement regions 130, 130' and 130" establish a positive operative connection with the positioning elements of the abutment stem (see radii R13, R12 in FIG. 2) such that the abutment can be positioned in the implant in a rotationally stable fashion. In comparison with implants and abutments that were produced by means of a grinding operation, almost no rotational clearance remains between these two parts. The corner radii R2, R22 are arranged on the fitted cylindrical receptacle openings 14, 14' and correspond to additional corner radii arranged on an abutment stem (not shown in FIG. 1). A snug fit results between the fitted cylindrical receptacle openings 14, 14' and the corresponding fitting cylinders on the abutment stem. The corner radii R2 and R22 are referred to as so-called blind hole radii. In the embodiment of the invention illustrated in FIG. 1, an undercut 15 featuring corner radii R3 is arranged in the proximal direction referred to the engagement key 13 and to the fitted cylindrical receptacle opening 14. The corner radii R3 are referred to as so-called groove radii. When an abutment (not shown in FIG. 1) is connected to the implant, the groove radii correspond to corner radii arranged on fixing elements of the abutment stem.

The undercut 15 and the fixing element establish a positive operative connection such that the abutment is fixed in the implant in an axial direction.

In the preferred embodiment according to FIGS. 1(a)-(c), the corner radii R1, R11, R2, R22 and R3 are smaller than/equal to 0.15 mm, preferably smaller than/equal to 0.1 mm, particularly smaller than/equal to 0.05 mm.

FIGS. 2(a), (b) schematically show an embodiment of an abutment 2 of zirconium dioxide in the form of a partial illustration, wherein said abutment can be connected to the receptacle opening of the implant 1 according to FIGS. 1(a)-(c). These figures respectively show a partial illustration of the abutment. Only the head of the abutment 21 and parts of the abutment stem 22 with the positioning elements 23, 23', 23' are illustrated. Fixing elements, which are likewise arranged on the abutment stem, and other components of the abutment stem, which are realized in the form of fitting cylinders, are not shown. The positioning elements have corner radii R12 and R13.

The corner radii R1 and R11 arranged on the engagement regions 130, 130', 130" of the engagement key 13 correspond to the corner radii R12 and R13 of the positioning elements. The engagement regions 130, 130', 130" of the engagement key 13 and the positioning elements 23, 23', 23" of the abutment stem establish a positive operative connection such that the abutment 2 can be positioned in the implant 1 in a rotationally stable manner(not visible in FIG. 2).

Figure 2:
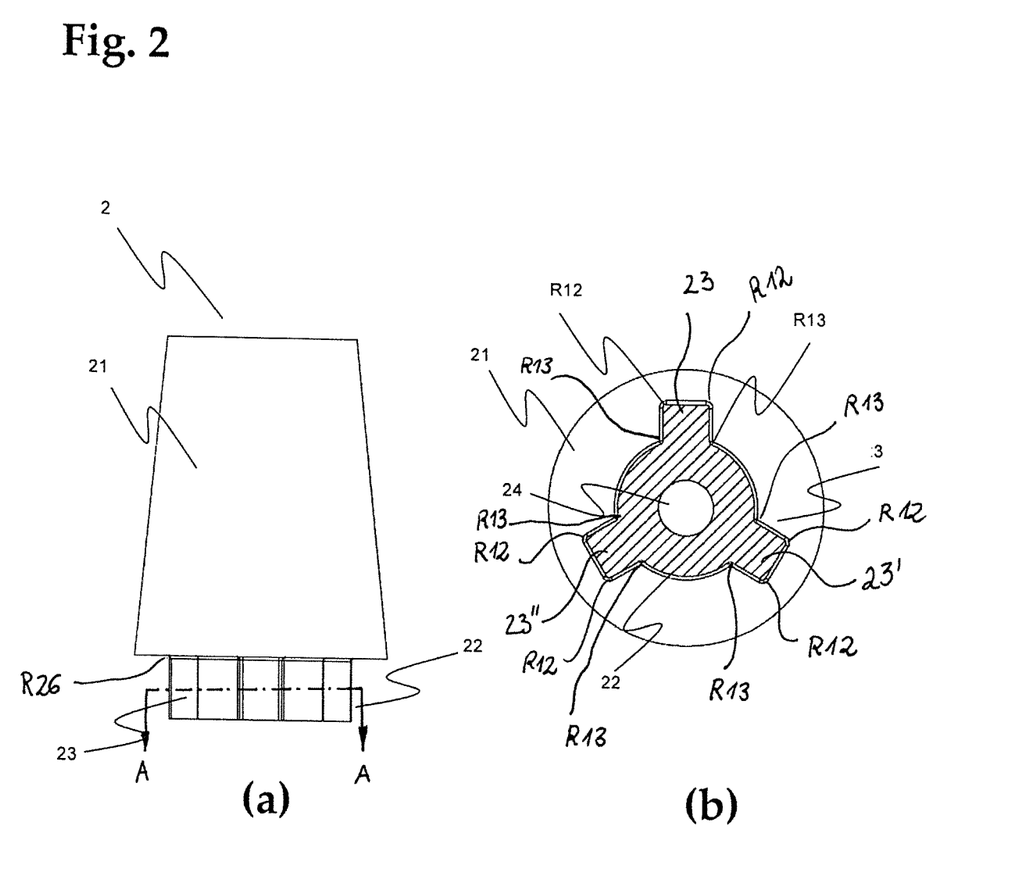
FIG. 2(a) shows a side schematic view of a milled embodiment of an abutment in the form of a partial illustration.
FIG. 2(b) shows a sectional schematic view of the milled embodiment of the abutment shown in FIG. 2(a), through the abutment in the region A-A of the abutment stem.

The corner radii R1, R11, R12 and R13 are smaller than/equal to 0.15 mm, preferably smaller than/equal to 0.10 mm, particularly smaller than 0.05 mm. The abutment stem 22 furthermore comprises an opening 24, for example, for accommodating a screw.

The abutment, particularly its abutment stem 22, was produced by means of a milling tool of full diamond and/or by means of a laser material removal operation using an ultrashort pulse laser.

Figure 3:
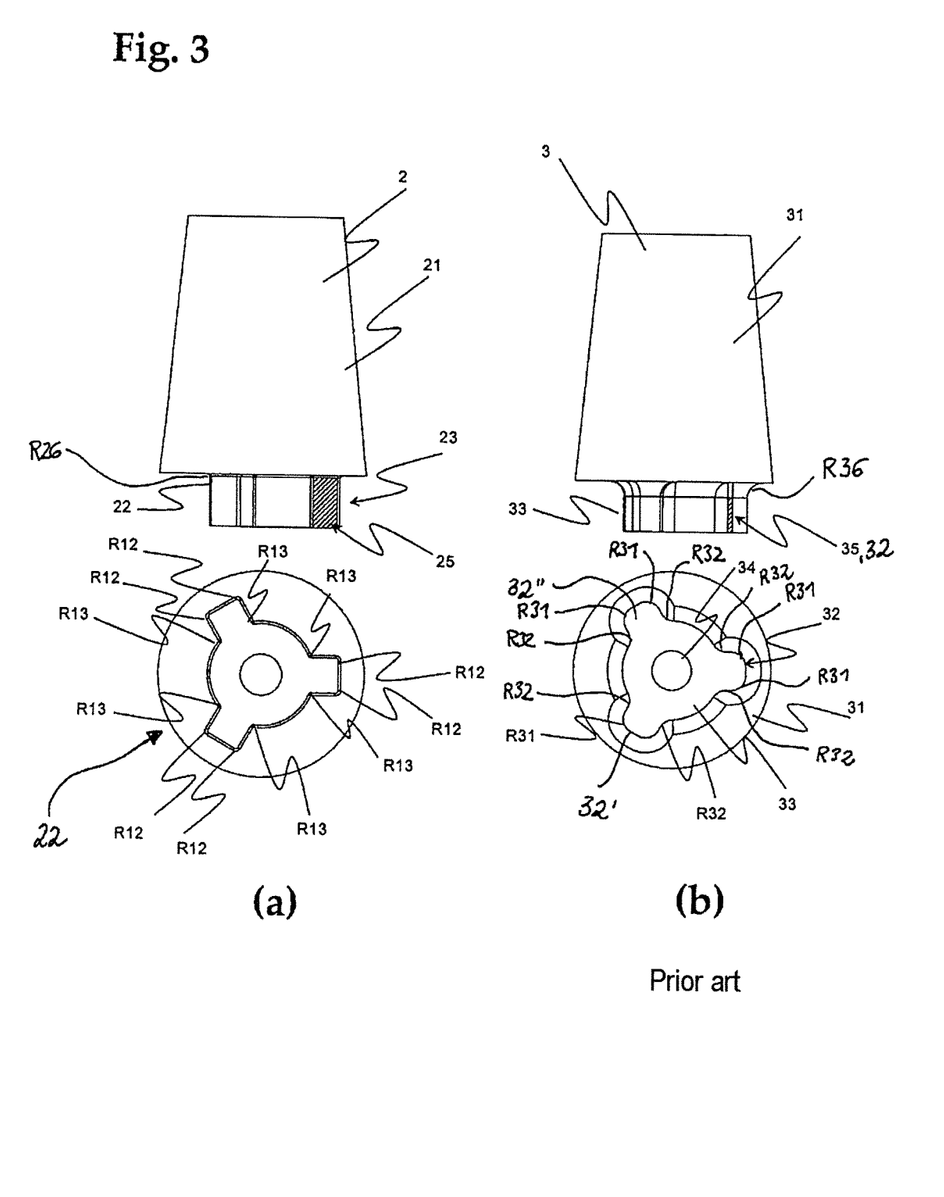
FIG. 3(a) shows another schematic side view of the abutment of the milled embodiment according to FIG. 2 in the form of a partial illustration, as well as a bottom view of the abutment stem and parts of the abutment head, under part (a).
FIG. 3(b) shows another schematic side view of the abutment of the milled embodiment according to FIG. 2 in the form of a partial illustration, and a side view of an abutment according to the prior art in the form of a ground embodiment, as well as a bottom view of the abutment stem and parts of the abutment head, wherein locking surfaces arranged on the abutment stem are illustrated with a hatching.

FIG. 3(a) shows the abutment 2 according to FIG. 2 in the form of another side view and another bottom view of the abutment stem 22 and the head of the abutment 21. In comparison with the illustration in FIG. 2, a locking surface 25 (illustrated with a hatching), which is arranged on one of the three positioning elements 23, 23', 23", is visible in the view according to FIG. 3(a).

FIG. 3(b) shows a similar view of an abutment as FIG. 3(a), but the desired shape of the abutment was in this case produced by grinding the zirconium dioxide body. The resulting geometry of the abutment is known from the prior art. This figure shows a side view of the abutment 3 with an abutment head 31 and an abutment stem 33. A locking surface 35 (illustrated with a hatching), which is arranged on these positioning elements 32, 32', 32", is likewise visible in this figure. The corner radii R31 and R32 arranged on these positioning elements 32, 32', 32" are visible in the illustration of the abutment 3 in the form of a bottom view. Analogous to the abutment according to FIG. 3(a), these corner radii are the so-called indexing radii.

A comparison between the inventive abutment 2 and the geometry known from the prior art elucidates the advantage of small corner radii, in the present example the small indexing radii R12, R13 in comparison with R31 and R32.

The indexing radii R12, R13 were produced by means of an ultrashort pulse laser and/or by means of a milling operation using a full diamond tool. The radii R31 and R32 in FIG. 3(b) were produced by means of grinding.

Indexing radii R12, R13, R31, R32 are provided on the abutment stem 22, 33, as well as in the receptacle opening of the implant (see R1, R11 in FIG. 1). The abutment stem comprises an opening 34 that serves for additionally fixing the abutment 3 in an implant. When the abutment 2, 3 is connected to the implant, the positioning elements 23, 23', 23", 32, 32', 32" engage into the engagement regions 130, 130', 130" of the engagement key and establish a positive operative connection. The corner radii R12, R13 and the corner radii R1 and R11 correspond in the inventive embodiment according to FIG. 3(a). A rotational clearance between the abutment and the implant, which on average amounts to 5° with ground radii, can be reduced on average by a factor of 5 by producing the corner radii arranged on the engagement key and on the positioning elements by means of a laser and/or by means of a machining operation using a drill or milling cutter of a full diamond.

The locking surfaces 25 (illustrated with a hatching), which correspond to locking surfaces arranged on the engagement regions 130, 130', 130" of the engagement key, are available for the rotationally stable positioning. Due to the very small corner radii of less than 0.15 mm, preferably less than 0.1 mm, correspondingly large locking surfaces 25, 25', 25" remain on the positioning elements 23, 23', 23". This likewise applies to the surfaces of the corresponding engagement regions of the engagement key in the implant. The larger locking surfaces achieved due to the smaller corner radii allow a stable connection and an improved force transmission between the abutment and the implant.

A comparison between the geometry of the abutment 3 and the geometry of the abutment 2 shows that the locking surface 35 is significantly smaller. The abutment 3 was produced by means of conventional grinding operations known from the prior art.

The corner radii R31 and R32, which in contrast to the corner radii R12 and R13 were ground into a zirconium dioxide blank, are correspondingly larger such that smaller locking surfaces 35 remain on the positioning elements of the abutment. This has disadvantageous effects on the rotationally stable positioning of the abutment in the implant.

According to FIGS. 3(a) and 3(b), outside radii R26 and R36, R26, which extend between the abutment stem 22, 33 and the abutment head and were produced by means of a machining operation using an ultrashort pulse laser, have a value of less than 0.15 mm, preferably less than 0.1 mm. When the abutment 2 is connected to an implant, the head 2 is seated on the implant (implant not visible in FIGS. 3(a), (b)) due to the small corner radii R26 and only a minimal circumferential gap results between the abutment head and a circumferential, distally arranged edge of the implant.

This is not the case in the embodiment of an abutment, which is machined by means of a grinding operation in accordance with the prior art. The radius R36 amounts to at least 0.2 mm. As a result, the abutment is not seated on the circumferential, distally arranged edge of the implant when it is inserted therein and an undesirable large gap is formed between the abutment head and the implant.

Figure 4:
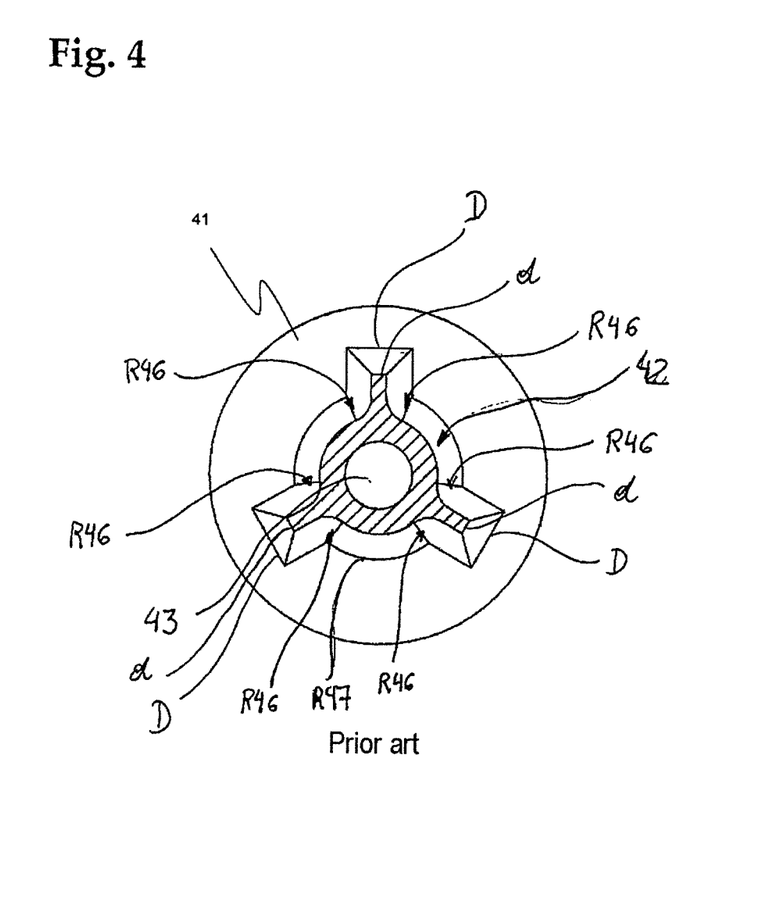
FIG. 4 shows another comparative example of a ground embodiment of an abutment known from the prior art in the form of a schematic bottom view of the cross section of an abutment stem and parts of the abutment head.

FIG. 4 schematically shows another ground embodiment of an abutment according to the prior art.

This figure shows a bottom view of the abutment with the abutment head and the adjacent abutment stem 42. The corner radii R46 are outside radii. The radius R47 is not a corner radius, but rather a radius of the abutment stem 42 itself. In this embodiment, an exemplary outside radius of 0.3 mm was ground into the abutment stem 42. However, it is very difficult to economically and technically implement corner radii below this value by means of grinding operations. Since the corner radii are produced by means of grinding operations, the material thickness of the abutment stem 42 is reduced from "D" at the outlet from the abutment head to "d" in the cross section shown. When this abutment is connected to the implant, a rotational clearance between the abutment stem and a receptacle opening in the implant (not shown in FIG. 4) results due to the reduction of the cross-sectional area, which is schematically indicated with "D" and "d." This rotational clearance is undesirable. The reference symbol 43 identifies a through-bore in the abutment stem 42 that serves, for example, for accommodating a connecting screw. Due to the reduction of the material thickness during the grinding operation of the corner radii, the cross-sectional area of the abutment stem is reduced such that a fracture of the abutment stem cannot be precluded.

Example of Calculation

If it is assumed, for example, that D=0.778 mm in the region of the outlet of the abutment stem 42 from the head 43 and a corner radius R46 of 0.3 mm is produced by means of a grinding operation, the value for d only amounts to 0.178 mm.

A comparison between the two geometries known from the prior art, which are illustrated in FIG. 3(b) and FIG. 4, once again elucidates the restrictions in the design freedom of dental prosthesis systems that are made of zirconium dioxide and are machined by means of grinding.

When the abutment illustrated in FIG. 4 is connected to an implant, it would be seated on a distal circumferential edge of the implant in the desired fashion because the radius R46 was ground to the required dimension. However, the cross section of the abutment stem would have been reduced due to the material removal to such a degree that the stability of the abutment in the implant can no longer be ensured.

In FIG. 3(b), the positional stability and the material stability in the inserted state of the abutment stem 33 into an implant is in fact ensured, but an undesirable gap results between a distally arranged edge of the implant and the abutment head in this state.

The invention claimed is:

1. A dental prosthesis system comprising:
a first and a second dental prosthetic care part (1, 2) made of sintered zirconium dioxide ($ZrO_2$), wherein both care parts respectively include corner radii (R1, R11, R2, R22, R3, R26, R12, R13), and wherein these corner radii (R1, R11, R2, R22, R3, R26, R12, R13) correspond to one another in that the first care part (1) is operatively connected to the second care part (2), wherein at least one of the corner radii (R1, R11, R2, R22, R3) of the first dental prosthetic care part and/or the second dental prosthetic care part (R26, R12, R13) comprises a corner radius of concave geometry with a value of less than or equal to 0.15 mm between and connecting two perpendicular walls of the first dental prosthetic care part and/or the second dental prosthetic care part, wherein the corner radii (R1, R11, R2, R22, R3, R26, R12, R13) are produced by means of a material removal operation using a laser and/or a machining operation using a drilling tool and/or milling tool of full diamond or cubic boron nitride.

2. The dental prosthesis system according to claim 1, wherein the corner radius lies in a range between 0.05 mm and 0.1 mm.

3. The dental prosthesis system according to claim 1, wherein the at least one corner radius has a shape that is sloped relative to a horizontal plane by 45°.

4. The dental prosthesis system according to claim 1, wherein the first dental prosthetic part is an implant (1) and the corner radii (R1, R11, R2, R22, R3) of the implant correspond to the corner radii (R26, R12, R13) of the at least one second dental prosthetic care part, wherein the second dental prosthetic care part comprises an abutment (2).

5. The dental prosthesis system according to claim 4, wherein the corner radii (R1, R11, R2, R22, R3) of the implant (1) are formed by inner walls of a receptacle opening of the implant and the corner radii (R26, R12, R13) of the abutment are arranged on an abutment stem.

6. The dental prosthesis system according to claim 5, wherein the inner walls form an engagement key (13) and the abutment stem comprises positioning elements (23, 23', 23"), wherein the corner radii (R1, R11) of the engagement key (13) and the corner radii of the positioning elements (R12, R13) correspond and the engagement key establishes a positive operative connection with the positioning elements such that the abutment (2) can be positioned in the implant (1) in a rotationally stable manner.

7. The dental prosthesis system according to claim 5, wherein the inner walls of the receptacle opening form an undercut (15) and the abutment stem comprises fixing elements, wherein the corner radii of the undercut (15) and the corner radii of the fixing elements correspond and the undercut (15) establishes a positive operative connection with the fixing elements such that the abutment (2) can be fixed in the implant (1) in an axial direction.

8. The dental prosthesis system according to claim 5, wherein the receptacle opening of the implant (1) comprises a circumferential edge with a corner radius, which is located in the distal direction.

9. The dental prosthesis system according to claim 4, wherein the inner walls of the receptacle opening form at least one fitting cylinder opening (14, 14') and the abutment stem comprises a fitting cylinder, wherein the corner radii of the fitting cylinder opening (14, 14') and the fitting cylinder correspond and the fitting cylinder and the fitting cylinder opening (14, 14') establish a positive operative connection such that a snug fit results between the two fitting cylinders.

10. The dental prosthesis system according to claim 1, wherein a corner radius (R26) extends circumferentially on the transition between the abutment head (21) and the abutment stem (22).

11. A method for producing a dental prosthesis system according to claim 1, wherein the shape of the base bodies of the dental prosthetic care parts (1, 2), and the shape of the desired corner radii (R1, R11, R2, R22, R3, R26, R12, R13), are produced by removing the zirconium dioxide material by means of an ultrashort pulse laser.

12. The method for producing a dental prosthesis system according to claim 11, wherein the corner radii (R1, R11) of the engagement key (13) of the implant (1) and the corner radii (R12, R13) of the positioning elements (23, 23', 23") of the abutment (2) are produced by removing the zirconium dioxide material with the aid of a picosecond laser.

13. A method for producing the dental prosthesis system according to claim 1, wherein the shape of the base bodies of the dental prosthetic care parts (1, 2), including the shape of the desired corner radii (R1, R11, R2, R22, R3, R26, R12, R13), is produced with a drilling tool and/or milling tool of full diamond or cubic boron nitride.

14. The method for producing the dental prosthesis system according to claim 13, wherein the base bodies of the dental prosthetic care parts (1, 2) are machined in another step by means of a material removal operation using an ultrashort pulse laser.

15. The method for producing the dental prosthesis system according to claim 13, wherein a milling head with a tool diameter of 0.5 mm to 5 mm or a side-and-face milling cutter with a tool diameter of 5 mm to 20 mm is used for the milling operation.

16. The method for producing the dental prosthesis system according to claim 15, wherein for a peripheral or a lateral milling operation for producing the corner radii of the second dental prosthetic care part <=15% of the tool diameter are laterally advanced when a milling head with a tool diameter of 0.5-1.5 mm is used or <=10% of the tool diameter are laterally advanced when a milling head with a diameter of 1.5-5 mm is used or <=10% of the tool diameter are laterally advanced when a side milling cutter with a tool diameter of 5-20 mm is used, wherein the depth of advance amounts to between 50 and 150% of the tool diameter.

17. The method for producing the dental prosthesis system according to claim 15, wherein for a groove milling operation for producing the corner radii of the first dental prosthetic care part a milling head with a tool diameter of 0.5-1.5 mm is used and advanced by an engagement depth of <=15% of the tool diameter or a milling head with a tool diameter of 1.5-5 mm is used and advanced by an engagement depth of <=7.5% of the tool diameter or a side-and-face milling cutter with a tool diameter of 5-20 mm is used and advanced by an engagement depth of <=5%, of the tool diameter wherein the lateral advance amounts up to 100% of the tool diameter.

18. The method for producing the dental prosthesis system according to claim 13, wherein a cutting speed of between 10-100 m/min, and an advance between 400-1200 mm/min, are chosen for a milling operation, and in that a cutting speed of 10-100 m/min and an advance between 5-75 mm/min are chosen for a drilling operation.

19. The dental prosthesis system according to claim 1, wherein the first dental prosthetic care part comprises an engagement region formed of four inner walls, the four inner walls each having an inner wall surface connected at a perpendicular angle to an abutting inner wall surface of an other of the four inner walls by a corresponding corner radius of concave geometry with the value of less than or equal to 0.15 mm.

20. A dental prosthesis system comprising:
 a first dental prosthetic care part made of sintered zirconium dioxide ($ZrO_2$), the first dental prosthetic care part comprising an engagement key including an engagement region formed of four inner walls each having an inner wall surface connected at a perpendicular angle to an abutting inner wall surface of an other of the four inner walls by one of a first plurality of corner radii each of concave geometry with a value of less than or equal to 0.15 mm;
 a second dental prosthetic care part made of the sintered zirconium dioxide ($ZrO_2$), the second dental prosthetic care part comprising an abutment stem including a positioning element with outer walls connected by a second plurality of corner radii and corresponding to the engagement region;
 wherein the first and second plurality of corner radii are produced by a material removal operation using a laser and/or a machining operation using a drilling tool and/or milling tool of full diamond or cubic boron nitride.

* * * * *